(12) United States Patent
Magidow

(10) Patent No.: US 9,098,732 B2
(45) Date of Patent: Aug. 4, 2015

(54) METHODS AND SYSTEMS FOR ANALYZING AND VISUALIZING SPRAY PATTERNS

(71) Applicant: Winfield Solutions, LLC, Shoreview, MN (US)

(72) Inventor: Lillian C. Magidow, St. Paul, MN (US)

(73) Assignee: WINFIELD SOLUTIONS, LLC, Shoreview, MN (US)

( * ) Notice: Subject to any disclaimer, the term of this patent is extended or adjusted under 35 U.S.C. 154(b) by 300 days.

(21) Appl. No.: 13/734,571

(22) Filed: Jan. 4, 2013

(65) Prior Publication Data
US 2014/0195948 A1 Jul. 10, 2014

(51) Int. Cl.
G06F 3/14 (2006.01)
G06K 9/00 (2006.01)
A01N 25/00 (2006.01)

(52) U.S. Cl.
CPC . *G06K 9/00* (2013.01); *A01N 25/00* (2013.01)

(58) Field of Classification Search
CPC .................................... G06F 3/14; G06F 3/17
USPC .......... 715/200–277, 700–867; 424/408, 739; 111/118; 345/30–111; 504/148, 255
See application file for complete search history.

(56) References Cited

U.S. PATENT DOCUMENTS

| | | | |
|---|---|---|---|
| 6,797,673 B1* | 9/2004 | Worthley et al. | 504/148 |
| 2004/0137031 A1* | 7/2004 | Seitz et al. | 424/408 |
| 2006/0034504 A1 | 2/2006 | Farina | |
| 2008/0121228 A1 | 5/2008 | Smyth et al. | |
| 2008/0187607 A1* | 8/2008 | Bessette | 424/739 |
| 2009/0241817 A1* | 10/2009 | Eastin et al. | 111/118 |
| 2010/0121620 A1 | 5/2010 | Schick et al. | |
| 2010/0185364 A1 | 7/2010 | McClure | |
| 2012/0166111 A1 | 6/2012 | El Giheny et al. | |
| 2013/0045869 A1* | 2/2013 | Liu et al. | 504/255 |

OTHER PUBLICATIONS

International PCT Search Report dated Apr. 11, 2014 for International Application No. PCT/US2013/076594.
Ground Spray Mobile Application, "Spraying Insecticide? There's an App for That", USDA, Agricultural Research Service, University of Nebraska-Lincoln, Mobile Phone Application, Nov. 2012. (search app store for "ground spray").
"AAT Aerial Sprays Simulator" and AAT Vector Spray, Aerial Spray Nozzle Models Mobile Applications, Aerial Application Technology Team, USDA, Agricultural Research Service, Dec. 2012. (search app store for "aerial spray").
"SpraySelect", TeeJet Technologies, Mobile Phone Application, date unknown.
"Tip Wizard Computerized Spray Tip Finder", Wilger Industries Ltd., Mobile Phone Application, www.tipwizard.net, date unknown.
"Nozzle Selector", Hardi International, "International Nozzel Calibration", Mobile Phone Application, www.hardi-nozzles.com, date unknown.

* cited by examiner

*Primary Examiner* — Ruay Ho
(74) *Attorney, Agent, or Firm* — Dorsey & Whitney LLP; Bridget M. Hayden, Esq.

(57) ABSTRACT

Computer-implemented systems and methods predict behavior of sprays based on receiving a selection of one or more variables affecting spray. Relative amounts of the droplets forming the spray are grouped into various droplet size classes, where each droplet size class represents a range of droplet sizes. The relative amounts of the spray in the classes is visually depicted on a computer display according to a distribution of droplets, a volume of spray falling within the droplet size classes, a chart depicting relative amounts of the spray as a function of droplet size, or according to a spray quality based on environmental factors.

20 Claims, 9 Drawing Sheets

```
┌─────────────────────────────────────────────────────────────┐
│ ANALYZING SPRAY PARTICULATE DATA OF SPRAYED FLUIDS TO       │──110
│ IDENTIFY A DROPLET SIZE DISTRIBUTION OF THE SPRAYED FLUIDS  │
└─────────────────────────────────────────────────────────────┘
                              ▼
┌─────────────────────────────────────────────────────────────┐
│ GROUPING THE ANALYZED SPRAY PARTICLES IN THE DISTRIBUTION   │──120
│                  INTO DROPLET SIZE CLASSES                  │
└─────────────────────────────────────────────────────────────┘
                              ▼
┌─────────────────────────────────────────────────────────────┐
│   CALCULATING A RELATIVE AMOUNT OF THE SPRAY WITHIN THE     │──130
│                     DROPLET SIZE CLASSES                    │
└─────────────────────────────────────────────────────────────┘
                              ▼
┌─────────────────────────────────────────────────────────────┐
│   RECEIVING A SELECTION OF THE SPRAYED FLUIDS WITH THE      │──140
│              ANALYZED SPRAY PARTICULATE DATA                │
└─────────────────────────────────────────────────────────────┘
                              ▼
┌─────────────────────────────────────────────────────────────┐
│  DISPLAYING CALCULATED RELATIVE AMOUNTS OF THE SPRAY        │──150
│  WITHIN THE DROPLET SIZE CLASSES BASED ON THE SELECTION     │
└─────────────────────────────────────────────────────────────┘
```

Fig. 1

METHODS AND SYSTEMS FOR ANALYZING AND VISUALIZING SPRAY PATTERNS

FIELD OF TECHNOLOGY

Methods and systems analyze and graphically display spray patterns based on user selections. More specifically, computer-implemented approaches enable users to observe differences in various spray patterns used in agricultural treatments based on the user's selections of spray variables.

BACKGROUND

Due to increasing concern about pest control costs and environmental pollution associated with agricultural sprays, application of such sprays requires precision and care. Considerable research on spray drift has been conducted, but it remains a major problem associated with many agricultural spray applications. Even when test data, for instance characterizing the drift potential or leaf coverage of an agricultural spray, are available, this information is difficult to communicate to individuals in systematic and easily understandable terms. Typically, spray patterns of agricultural sprays, such as pesticides, must be tested in order to provide individuals with desired result data; or where previously analyzed results are available, the information is required to be added to a custom presentation or report for the individual. In addition, spray patterns are affected by the type of nozzle used to deliver the spray, and nozzles must be tested or nozzle analysis results are required to be added to custom presentations. Further, other variables affecting spray such as environmental factors may not be available. Conducting these processes is time-consuming, test results may be incomplete due to unavailable information, and the results may not be delivered in a timely manner.

SUMMARY

In view of the foregoing, there is a need to provide an approach that rapidly delivers meaningful agricultural spray test data to users. Further, there is a need to provide an approach that allows users to select variables affecting spray patterns in order to understand and compare predicted spray patterns based on one or multiple agricultural treatments of interest.

The present disclosure, therefore, provides computer-implemented approaches that generate and display agricultural spray pattern information. This spray information displayed may be based on spray analyses, such as sprays analyzed using laser diffraction analysis. Users may enter selections including variables affecting a spray pattern such as composition, spray conditions and environmental factors, and a display may provide visual information about the analyzed spray pattern, its quality or acceptability.

In some aspects, a computer-implemented method for depicting agricultural spray behavior as a spray distribution involves using a computer processor, which receives selections of an agricultural spray and parameters at which the agricultural spray is to be sprayed. The processor retrieves analyzed spray particulate data based on the selections, which includes a distribution of relative amounts of agricultural spray droplets within droplet size classes, where each class corresponds to a range of droplet sizes. A computer display graphically displays the distribution of the relative amounts of the spray droplets in the droplet size classes and depicts the spray droplets as a series of representative droplets, where each representative droplet is associated with one of the droplet size classes. The representative droplets are arranged within a distribution curve representing a distribution of size of the representative droplets based on the relative amounts, thereby providing a visual display of a distribution of the droplet size of the selected sprayed fluid.

In other aspects, a computer-implemented method for depicting agricultural spray behavior involves using a computer processor, which receives selections of an agricultural spray and one or more parameters at which the agricultural spray is to be sprayed, and in response, retrieves analyzed spray particulate analysis data including relative amounts of agricultural spray droplets within droplet size classes corresponding to a range of droplet sizes. A computer display graphically displays the relative amounts of the spray droplets in the droplet size classes.

In further aspects, a computer-implemented method for providing agricultural spray information involves using a computer processor, which analyzes spray particulate data of sprayed agricultural fluids to identify a droplet size distribution of the sprayed fluids; groups droplets within the droplet size distribution into droplet size classes, where each droplet size class represents a range of droplet sizes; calculates a relative amount of the droplets within the droplet size classes; and receives a selection of an agricultural mixture corresponding to one of the sprayed fluids. A computer display of the calculated relative amounts of the droplets within the droplet size classes for the spray particulate data is displayed based on the received selection.

BRIEF DESCRIPTION OF THE DRAWINGS

FIG. 1 is a flow chart of a method for providing spray behavior information in a visual format.

DETAILED DESCRIPTION

Figure 2:
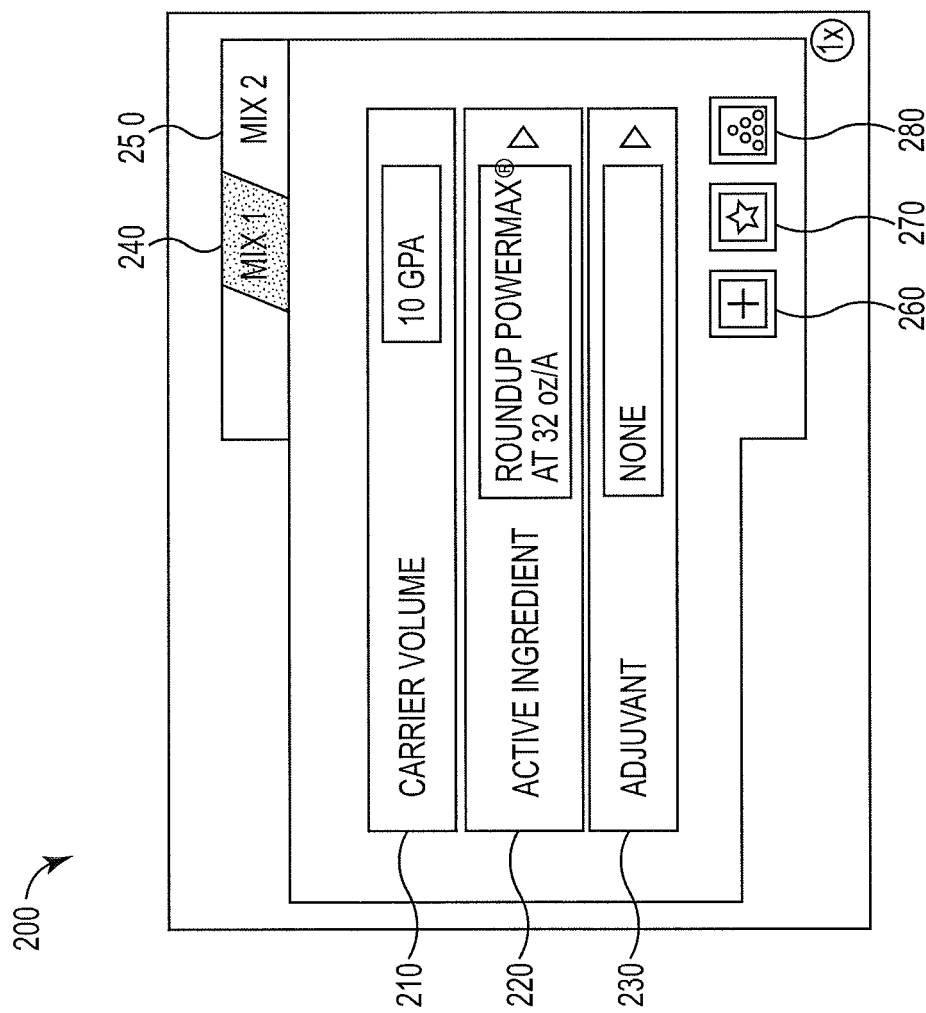
FIG. 2 depicts a user interface providing user-selectable fields for selection of spray parameters to be used in providing spray behavior information in a visual format.

Computer-implemented approaches provide spray visualization tools that enable users to select variables affecting spray patterns, such as for agricultural sprays, and view differences in sprays based on these selections. The disclosed approaches are useful in delivering spray analysis data in a user-friendly, visual format, which may educate users about predicted spray patterns according to spray parameters of interest and may allow users to refine spray parameters of interest based thereon. These implementations may additionally include information related to spray drift (e.g., off-target movement) due to wind speed and leaf coverage due to boom height. This may enable users to assess whether sprays will be effective for treating crops in certain environmental conditions.

FIG. 1 illustrates a flow diagram of a method 100 for providing spray information in a visual format, which may be useful in understanding the behavior of sprays composed of various components, such as agricultural components used in treating crops and soil. The method 100 may be implemented using the computer system of FIG. 7.

Method 100 may involve executing instructions using a computer processor for analyzing 110 spray particulate data of sprayed fluids to identify a droplet size distribution of the droplets defining the sprayed fluids. Analyzing spray particulate data 110 may involve receiving data from an analysis device configured to evaluate a sprayed fluid. For example, spray analysis methods may include laser diffraction analysis within a closed system, such as a wind tunnel spray analysis device.

The analyzed 110 spray particulate data may include a range of droplet sizes within the spray distribution. In addition, information identifying the analyzed sprayed mixture and additional variables that affect how the mixture is sprayed may be provided. This information may include: spray identification information, such as composition parameters, of the mixture including active ingredients and adjuvants; and additional spray parameters beyond the spray composition, such as delivery parameters, including active ingredient rates, adjuvants rates, spray pressure, rate of spray per acre (e.g., spray volume per acre), spray pressure (e.g., 20 psi, 40 psi), and nozzle type (e.g., XR11002, XR11003, and AIXR11002), as well as environmental parameters affecting spray, such as boom height and wind speed.

With respect to the aforementioned delivery parameters affecting spray, when the spray is analyzed using a fluid delivery system, including closed systems such as wind tunnels, these delivery parameters may be controlled and/or monitored during testing. For example, spray pressure may be monitored using the fluid delivery system and variations in pressure may be recorded to confirm that spray analysis is recorded while the spray is delivered at a selected pressure, which may ensure accurate spray behavior analysis information is documented. In another example, for mixtures sprayed through a nozzle, the spray produced from the mixture may be affected by the nozzle type as well as the composition in the mixture, e.g., pesticides and adjuvants, and these variables may be recorded during analysis. In some cases, the analyzed fluid may be water, such as when water is used as a baseline for comparison with agricultural sprays formed of active ingredients.

With respect to environmental parameters, such as boom height in ground spray applications, the boom height may be set close to the ground (e.g., 18 inches from the crop canopy) or at a slight elevation (e.g., 36 inches from the crop canopy), and these variations may affect whether a spray reaches its target (e.g., reaches leaves of agricultural crops) or whether the spray is at risk of drifting off-target. Wind speed may additionally affect whether the spray reaches its target. In some aspects, these environmental parameters affecting spray may be based on field studies and modeling, which may be in addition to other modes of spray analysis.

Method 100 continues by grouping 120 the analyzed spray particulates within the distribution into droplet size classes. Each of the size classes may represent a range of droplet sizes. The droplet size classes may be defined upon receiving the spray particulate data, or the droplet size classes may be predefined, for example, based on droplet sizes that may be at risk for drift, that may traditionally reach the intended target, and that may contribute to leaf runoff. In addition, the predefined droplet size classes, and the ranges for acceptable versus unacceptable droplet sizes, may differ based on the type of agricultural spray. Where a variety of size classes are available, one or more size classes may be selected based on the composition of the sprayed fluid, spray parameters and combinations thereof.

In one example, the droplet size classes may be divided into size ranges, such as, discrete ranges based on a volume median diameter ("VMD") of less than 136 μm, from 136 μm to 177 μm, from 178 μm to 218 μm, from 219 μm to 349 μm, from 350 μm to 428 μm, from 429 μm to 622 μm, and greater than 622 μm. The VMD is known as $Dv_{0.50}$ or $X_{50}$ and is typically characterized in micron units (μm). The VMD numeric value is the median droplet size of the spray such that half of the volume of the spray contains droplets smaller than the VMD and half of the volume contains droplets larger than the VMD. A smaller VMD may correspond to a fine spray and a larger VMD may correspond to a coarser spray.

In some aspects, the droplet size classes may be defined according to a spray's statistical moment, such as the median size (e.g., $X_{50}$) or $X_{10}$ (e.g., where 10 percent of the volume of spray is in droplets smaller than this value).

In additional aspects, the droplet size classes may be associated with a volume of the spray within a size class. For example, the percent of spray volume <105 um (V105) is defined as driftable fines by ASTM and may be valuable in characterizing the drift potential of a spray, and two classes may be defined for droplets falling below <105 μm (V105) and droplets falling above this value.

Figure 7:
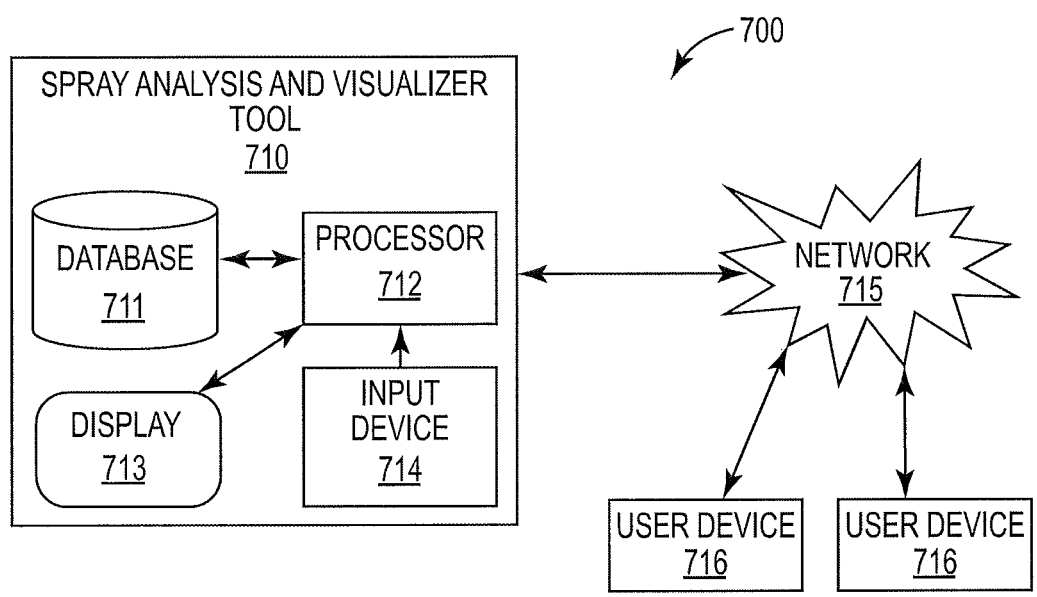
FIG. 7 is a block diagram of a computer system providing a spray visualization tool according to certain implementations.
Figure 8:
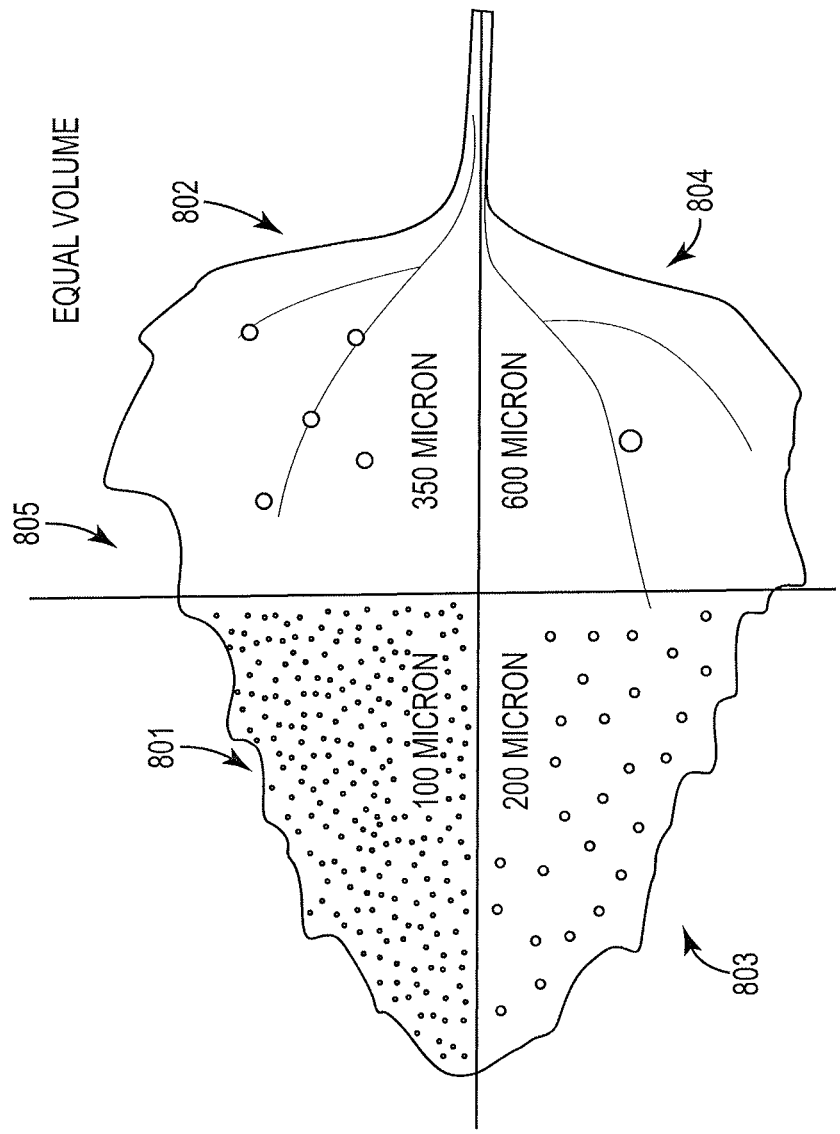
FIG. 8 depicts a visual representation of spray droplets on an agricultural target

The droplet size classes may additionally or alternatively be characterized by droplets per $in^2$ ("$dpi^2$") at a given application rate (such as 10 gallons per acre or GPA) such as greater than 4528 $dpi^2$, 2078 $dpi^2$, 1112 $dpi^2$, 271 $dpi^2$, 147 $dpi^2$, 48 $dpi^2$, and less than 48 $dpi^2$. In some examples, a VMD of the droplets may be used to approximate the $dpi^2$ value. In addition, the $dpi^2$ value may describe an upper limit of a droplet size class. In some aspects, the $dpi^2$ of a given spray may be depicted visually. For example, in FIG. 8, representative droplets for four different sprays 801-804 spray are superimposed over a weed leaf image 805 based on the maximum per-area leaf coverage (e.g., $dpi^2$) at their respective median particle size and carrier volume rate (e.g., gallons per acre). The median particle sizes may be retrieved from the computer system of FIG. 7 and the $dpi^2$ provided visually for each spray combination (e.g., for the combination of variables that affect a spray: active ingredients, adjuvants, spray pressure, carrier volume rate, and nozzle type). As shown in FIG. 8, while the volume of spray per square inch of leaf is the same for the four sprays, leaf coverage differs with differing $dpi^2$ levels. The visual representation of the spray may be linked to, or provided on, one or more of the user interfaces discussed below, or may be provided as a separate user interface. Although FIG. 8 represents a weed leaf image, the visual representation may be for any agricultural spray target such as a crop plant or crop plant leaf at various stages of growth. In addition, the $dpi^2$ visual representation may be displayed on the agricultural target on a per spray basis, or may be displayed side-by-side for comparison of sprays. Further, in addition or as an alternative to displaying the spray on a $dpi^2$ basis, the spray may be displayed on a VMD or another droplet size class basis.

The size classes may additionally or alternatively be assigned spray qualities such as very fine ("VF"), fine ("F"), medium ("M"), course ("C"), very course ("VC"), extra course ("XC") and ultra course ("UC"). For example, the spray qualities may be based on droplet size classifications used in the industry, such as Spraying Systems TeeJet Technology Catalog 51. The spray qualities may be color-coded by the ASABE S572.1 test method. In some applications, the spray qualities may be associated with one or more of the VMD ranges. Further, the classes may be assigned a drift potential rating such as from high to low drift potential.

In some implementations, prior to grouping 120 the analyzed spray particulates into classes, the overall particulate count may be reduced. For example, the count of droplets may be represented as one hundred millionth ($1\times10^{-8}$) of the droplets present in 10 gallons of liquid.

In method 100, the relative amount of the spray within the droplet size classes may be calculated 130, which may identify an overall distribution of the spray particulates within the spray. Calculating relative amounts of spray may involve one or both of calculating a volume of the spray within the classes or calculating a count of droplets within the classes. For example, a percentage of the spray volume or a percentage of spray droplets falling within the droplet size classes of the present disclosure for a variety of sprays may be calculated 130. In one example, the percent spray volume falling below and above 105 μm may be calculated for various sprays, which may identify the percentage of driftable fines within such sprays.

In some aspects, the droplet sizes, droplet size classes and calculated relative amounts of the droplets, droplets and volume within the classes, other spray analysis information, and combinations and variations thereof may be stored in a database, such as the database of the computer system of FIG. 7.

Method 100 continues by receiving 140 selections identifying the sprayed fluids associated with the spray particulate data. The selection may be a user selection of one or more variables affecting spray such as spray composition parameters, including active ingredients and adjuvants; and spray parameters including delivery parameters, such as spray pressure, carrier volume rate (e.g., gallons per acre ("GPA" such as 10 GPA), product use rate (e.g., pesticide use rate, adjuvant use rate, or combinations), nozzle type, and environmental parameters, such as boom height and wind speed. For example, the selection may be one or more of an active ingredient and an adjuvant along with a selection of one or more of a rate of spray (e.g., carrier volume), a nozzle type and a spray pressure. In a further example, the selection may include one or more of a wind speed or boom height at which the spray is delivered. In some implementations, the received selection may be a user selection obtained from one or more user interfaces, such as from the user interfaces illustrated in FIGS. 2-6 of the present disclosure.

Based on the received selection 140, the calculated relative amounts of the spray within the droplet size classes for the spray particulate data may be retrieved from a database and displayed 150 on a computer display. For example the spray may be depicted as spray droplets representing droplet size ranges or may be depicted as a spray volume of the spray droplets falling within the droplet size ranges. Particularly, the spray characteristics may be depicted using a variety of display types, such as via the user interfaces illustrated in FIGS. 3A-6 of the present disclosure. In aspects where the overall particulate count is reduced, the full count population of the droplet reduction may be depicted on the computer display.

Turning to FIG. 2, a user interface 200 displays user-selectable fields for entering spray variables used in providing spray analysis results in a visual format. The selectable fields in FIG. 2 include a carrier volume 210 corresponding to a spray volume per acre, such as gallons per acre; an active ingredient 220 corresponding to crop treatment chemicals (e.g., active ingredients) such as one or more pesticides; and an adjuvant 230 corresponding to one or more surfactants, crop oil concentrates, nitrogen fertilizers, spreader-stickers, wetting agents, penetrants and so on. The spray mixture selection depicted in FIG. 2 represents a first selected mixture, and a first user-selectable area "Mix 1" 240 enables the user to select and view the spray variables for the first mixture. A user may toggle between spray selections for another mixture "Mix 2" by selecting a second user-selectable area "Mix 2" 250. A user interface for "Mix 2" may be substantially similar to the user interface 200 of FIG. 2, thereby enabling a user to select two different sprays for comparison. In addition, the user may add selections for "Mix 1" or "Mix 2" as a preferred or favorite spray by selecting the plus icon 260, and may recall the added selection by selecting the star icon 270. Although FIG. 2 provides three selectable fields for identifying a spray variables for a mixture to be analyzed, the user interface 200 may provide more or less fields for such identification, and the fields may correspond to any of the variables affecting spray according to the present disclosure. In addition or alternatively, constant values may be assigned to one or more variables affecting spray. In use, once a user has entered mixture selections for a spray, or two or more sprays for comparison, the analyze icon 280 may be selected for review of a spray analysis of the selected spray, or for a comparison of the analysis for the selected sprays.

FIG. 3A depicts a user interface 300 providing a distribution view 301 of a selected spray illustrating how spray variables affect spray behavior with respect to the spray's distribution. The distribution view 301 may be provided in connection with aspects of the method 100 of FIG. 1, and user selections of spray variables for displaying the distribution view 301 may be received via the user interface 200 of FIG. 2 as well as the user interface 300. The distribution view provides a visual depiction of a population of sprayed droplets based on a selected spray, such as the first spray mixture "Mix 1" 302. The components of the spray mixture of "Mix 1" may be displayed, such as a mixture of a pesticide at 22 oz. per acre at 10 gallons per acre. In some aspects, selections may be entered via user interface 300 related to the mode of spray delivery of the first spray mixture, such as delivery from a particular nozzle. For example, the nozzle field 305 may receive a selection identifying a nozzle type (e.g., XR11003, AI11005 or another nozzle type) through which the spray will be delivered. The mode of spray may be additionally or alternatively tailored using the pressure field 310, which may receive selections identifying a specified pressure (e.g., 30 psi, 40 psi, or 50 psi,) at which the spray will be delivered.

In some aspects, selection of the analyze icon 315 following selection of the spray variables results in displaying the distribution view 301. For example, the distribution view 301 in FIG. 3A is depicted as a series of representative droplets 320 that may be generated by predicting the relative amounts of the droplets within the droplet size classes when the first mixture is sprayed using the selected nozzle at the selected pressure. Each representative droplet displayed may be associated with one of the droplet size classes of the present disclosure and may represent a predetermined volume of spray. For sprays having a large volume of spray falling within the droplet size class, a larger number of the representative droplets may be displayed compared to another droplet size class having a relatively smaller volume of spray.

In further aspects, the representative droplets within the droplet size class may be displayed with droplet size information 325 indicative of the range of droplet sizes for the representative droplet such as range of droplet sizes represented, e.g., according to droplet diameter; drift potential, e.g., where smaller droplets are at risk of particle drift; and leaf runoff potential, e.g., where large droplets are at risk of bouncing and running off of leaves. The droplet size information 325 may be displayed by selecting or "hovering" over the representative droplet.

The representative droplets 320 within the distribution view 301 may be arranged within a distribution curve 330 representing a distribution of size of the representative droplets based on the relative amounts of the droplets within the droplet size classes. This may provide a visual display of a distribution of the droplet size of the selected sprayed fluid. Further, within each size class, the size of the representative droplets 320 may be the same, but across classes, the representative droplet size may vary. This may further provide a user with a visual indication of the spray volume across the distribution curve 330 based on droplet size class.

In addition, the user interface 300 may display a span value 335 of the distribution of the spray. The span value 335 is a relative span of the spray:

$(X_{90}-X_{10})/X_{50}$, where $X_{90}$ indicates that 90 percent of the volume of spray is in droplets smaller (or 10 percent larger) than this value, $X_{10}$ indicates that 10 percent of the volume of spray is in droplets smaller than this value, and $X_{50}$ is the volume median diameter of the spray. An example of a span calculation is where $X_{50}$ is 200 µm, $X_{90}$ is 500 µm and $X_{10}$ is 260 µm, giving a span of ([500−260]/200)=1.3. Generally, a relatively higher span value represents a variable spray pattern, whereas a relatively lower span value represents a more consistent spray pattern. For example, a span value of about 1.5 may be characterized as highly variable, a span value of about 1.0 may be characterized as a consistent spray and a span value of less than about 1.2 may be characterized as an ideal spray. Further, a VMD value 340 of the distribution may be displayed, and in FIG. 3A, the VMD value displayed is 179 µm.

In some aspects, a value within the particulate size field 345 may be selected and the system may calculate and display a percentage of spray value 350 for the portion of the spray droplets corresponding to the selected particulate size value. The particulate size field 345 may provide a variety of droplet sizes at which the system calculates the percentage of volume of particulates falling at, above or below the droplet sizes, or may provide a variety of droplet size ranges at which the percentage of particulates falling within the range may be calculated. In some aspects, the particulate size field 345 may provide a cumulative volume percent of percent fines or $V_n$, where the percent of spray volume is smaller than a given droplet size (n microns). Percent fines may be droplets smaller than 105 µm (e.g., based on ASTM Test Method E2798-11). For example, in FIG. 3A, the selected particulate size value in the particulate size field 345 is particulates that are smaller than 105 µm, and the percentage of spray value 350 containing droplets smaller than 105 µm is 17.8 percent. Percent fines may additionally or alternatively be droplets smaller than 210 µm, as droplets falling below this size may be considered subject to drift.

Using the various mix, analyze, spray and gallery icons 355, a user may toggle between various user interfaces provided according to the present disclosure. By selecting the switch icon 360, the system may toggle between distribution views of the selected spray mixtures. For example, as shown in FIG. 3B, the user interface 370 provides a distribution view 371 of the sprayed droplets from the spray in the second spray mixture "Mix 2" 372, and the user interface 370 may be displayed in response to selecting the switch icon 360 in FIG. 3A.

Figure 3A:
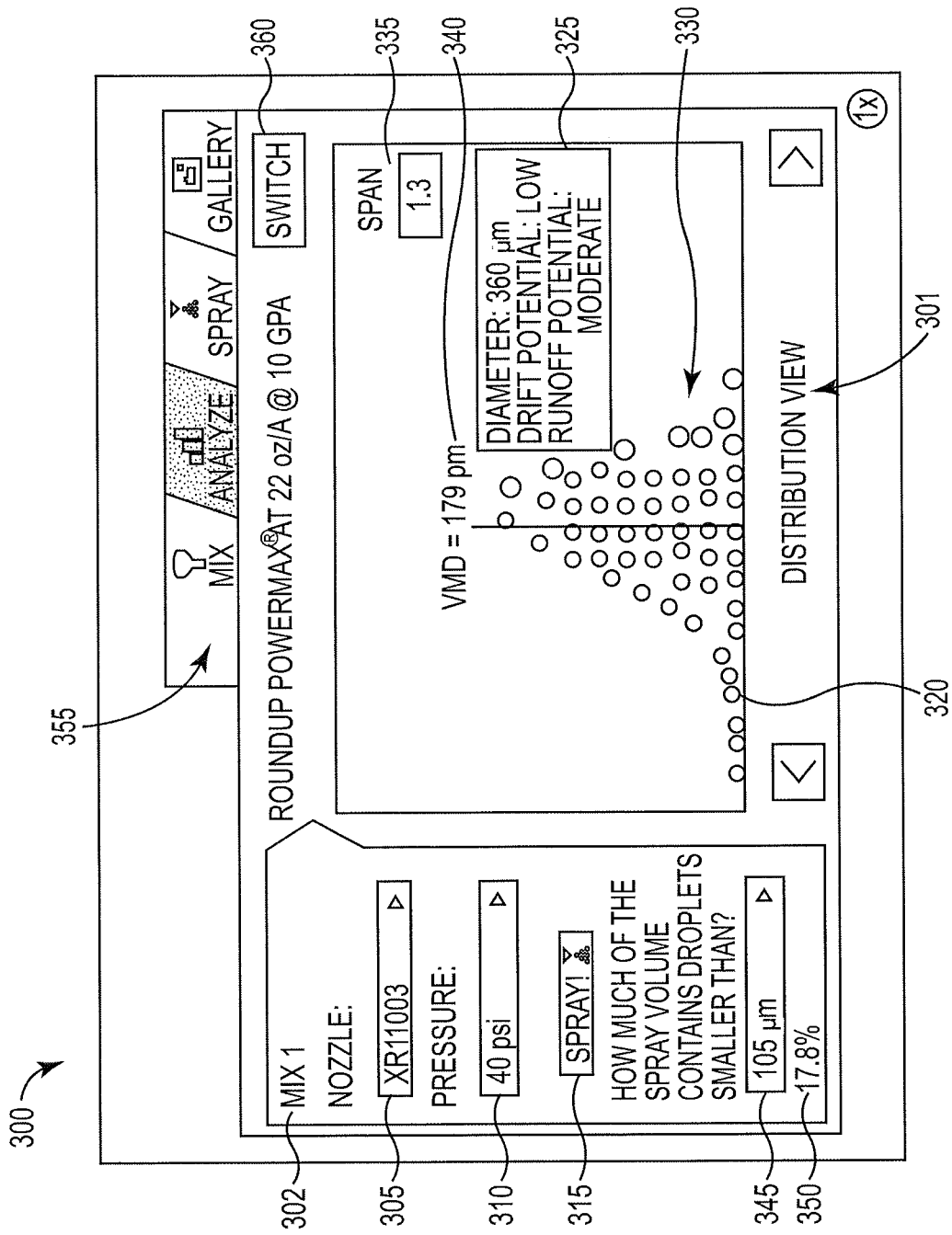
FIG. 3A depicts a user interface for providing a distribution view of a first spray.
Figure 3B:
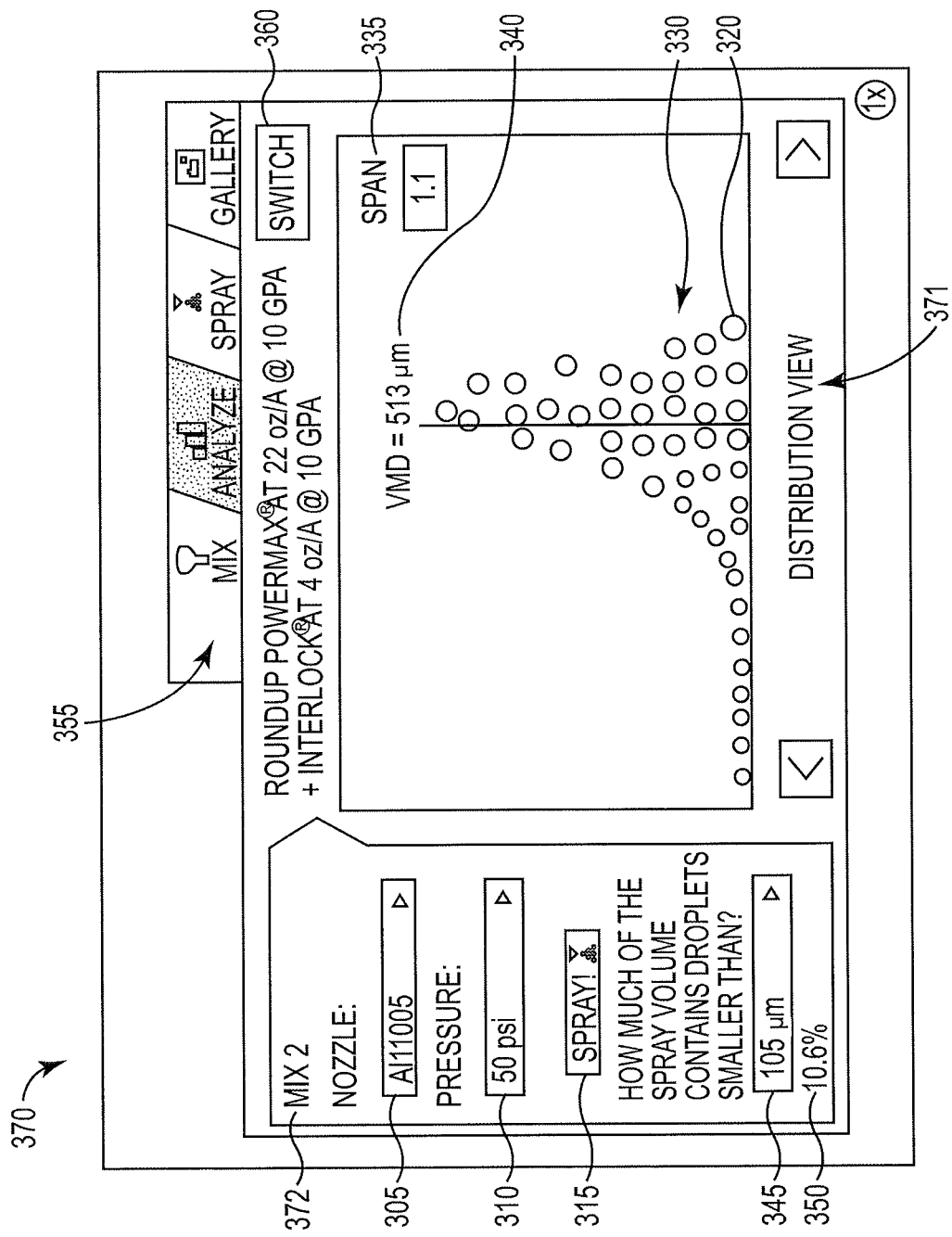
FIG. 3B depicts a user interface for providing a distribution view of a second spray.

A comparison of the distribution views 301, 371 of FIGS. 3A and 3B shows the distribution of the particulates differ visually, and that the span value 335 for the first mix is 1.3, whereas the span value 335 for the second mix is 1.1. In addition, the percentage of spray value 350 containing droplets smaller than 105 µm is 17.8 percent for the first mix, whereas this value is 0.6 percent for the second mix. Further, the VMD 340 for the first mix is 179 µm, while this value for the second mix is 513 µm. By comparing the distribution views 301, 371, relative differences between the sprays may be assessed, and based on the information displayed in FIGS. 3A and 3B, the second spray mixture "Mix 2" 372 is associated with a more consistent spray with its relatively smaller span value 335, a relatively higher VMD value 340 and less droplets with a size smaller than 105 µm.

Further, by receiving different selections for a spray or selecting from one or both of the nozzle field 305 and the spray field 310, and by selecting the analyze icon 315, a new distribution view for the new selection may be displayed on the user interface 300, 370.

Figure 4:
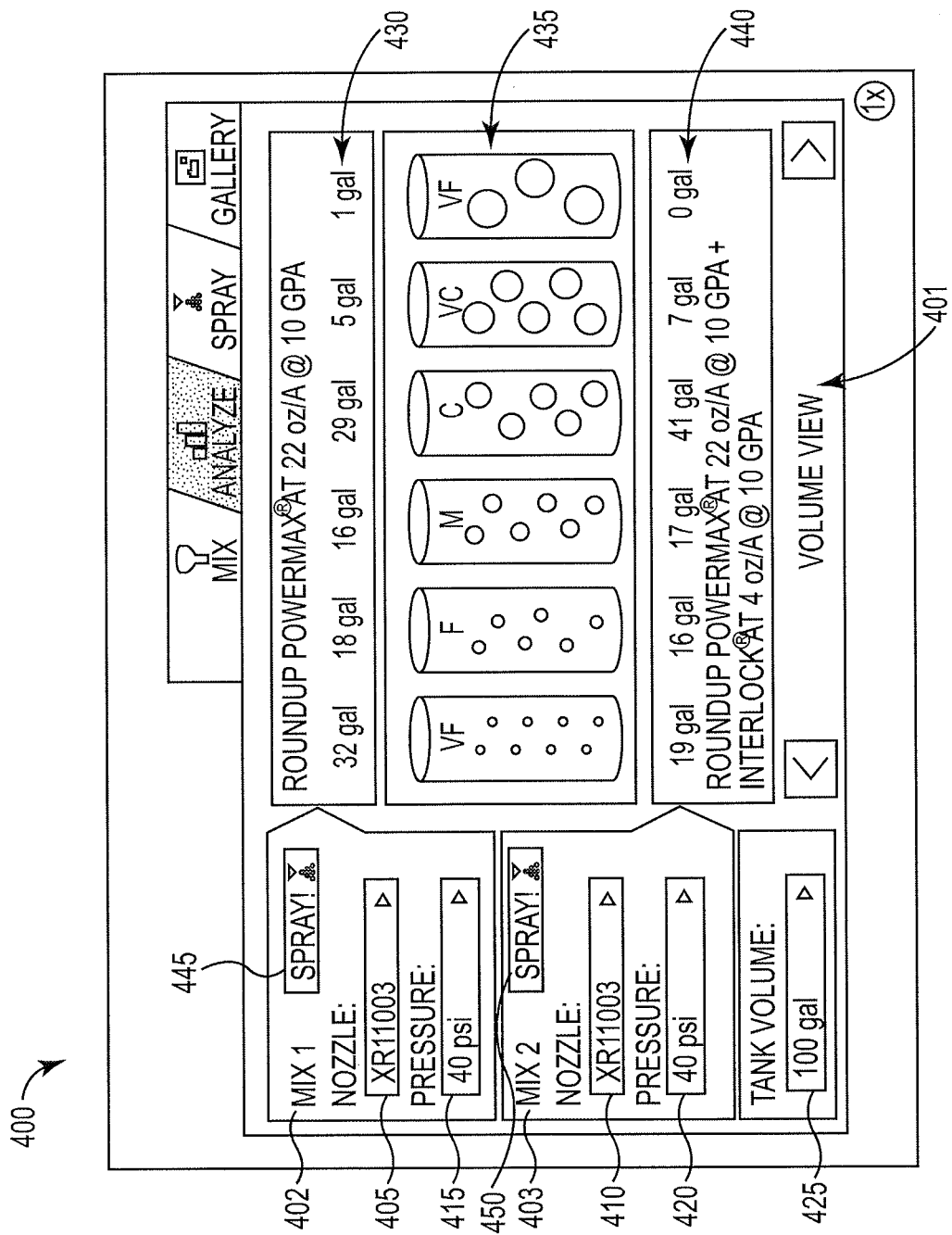
FIG. 4 depicts a user interface for providing a volume view of a first and second spray.

FIG. 4 depicts a user interface 400 illustrating a volume view 401 of a first and second selected spray, "Mix 1" 402 and "Mix 2" 403. This spray behavior view may be may be provided in connection with aspects of the method 100 of FIG. 1, and selections for the two different sprays may be received via the user interface 200 of FIG. 2 for "Mix 1" 402, and via a second user interface for "Mix 2" 403, described above, as well as via user interface 400. The volume view 401 may provide a calculation of the spray volume for one or more sprays according to the droplet size classes of the present disclosure. In some aspects, selections may be received for two different sprays, such as sprays with differing active ingredients, adjuvants, or both, and the relative amounts of the droplets within the droplet size classes may be displayed as a volumetric comparison of the two different selections.

Using FIG. 4 as an example, the predicted spray falling within droplet size classes produced by the "Mix 1" 402 components may be compared against the "Mix 2" 403 components. The spray components may be based on selections such as the active ingredient, adjuvant and spray volume selections from FIG. 2. The mixes 402, 403 in this example are formed of different components in which "Mix 1" is formed of a pesticide and "Mix 2" is formed of the same pesticide along with an adjuvant, and the user interface 400 receives selections of the same nozzle (e.g., XR11003) and pressure (e.g., 40 psi) via the selectable nozzle fields 405, 410 and the selectable pressure fields 415, 420 for each of the mixes 402, 403. Based on the selections, the calculated relative amounts of the droplets falling within the droplet size classes for each of the mixes may be displayed on a per volumetric unit basis. In FIG. 4, the relative amounts within each class are displayed on a per gallon basis based on receiving a selection from the tank volume field 425 of 100 gallons. For "Mix 1" 402, the relative amounts of the spray within the classes 430 are displayed above the droplet size class categories 435 (e.g., VF (very fine), F (fine), M (medium), C (course), VC (very course) and UC (ultra course)) proximate where "Mix 1" 402 is identified on the user interface 400. Similarly, for "Mix 2" 403, the relative amounts of the spray within the classes 440 are displayed below the droplet size class categories 435 proximate where "Mix 2" 403 is identified on the user interface 400. Because the only difference between the mixes 402, 403 and the conditions (e.g., nozzle type and pressure) at which the mixes are sprayed is the addition of the adjuvant in "Mix 2" 403, the volume view 401 displays the effect of the adjuvant has on the sprayed pesticide based on droplet size class category.

In further aspects, the user interface 400 of FIG. 4 may be used to compare sprays that are sprayed at different conditions. For example by receiving mix selections or spray condition selections different from that depicted in FIG. 4, in combination with receiving a selection of one or more of the spray icons 445, 450 for "Mix 1" 402 and "Mix 2" 403, respectively, the system may display a volume view for the new selection.

The user interface 400 of FIG. 4 may enable a user to determine whether a spray reaches its target, is lost (e.g., due to drift) or is ineffective (e.g., due to droplets falling off of the leaves). In further aspects, a user may determine the cost-effectiveness of a spray based on these determinations. For example, where the pricing of the mixture is stored or where the pricing is entered by a user, the cost-effectiveness of the sprays may be assessed. In addition, based on the volumetric results and depending on the type of active ingredient, e.g., pesticide, the system may characterize the sprays as acceptable or unacceptable or may rank the sprays relative to one another. For instance, some sprays such as those used in contact fungicide applications have recommended spray grades of medium (M), fine (F) and very fine (VF), and fungicide sprays with droplets falling within these grades may be characterized as acceptable. In contrast, for post-emergence herbicides having recommended spray grades of medium (M), course (C) and very course (VC), the herbicide sprays having grades within the fine and very fine grades may be characterized as unacceptable. Accordingly, aspects of the present disclosure may account for the different modes of action for these products, which may facilitate a user selecting variables affecting spray to achieve a desired level of leaf surface coverage or drift control.

Figure 5:
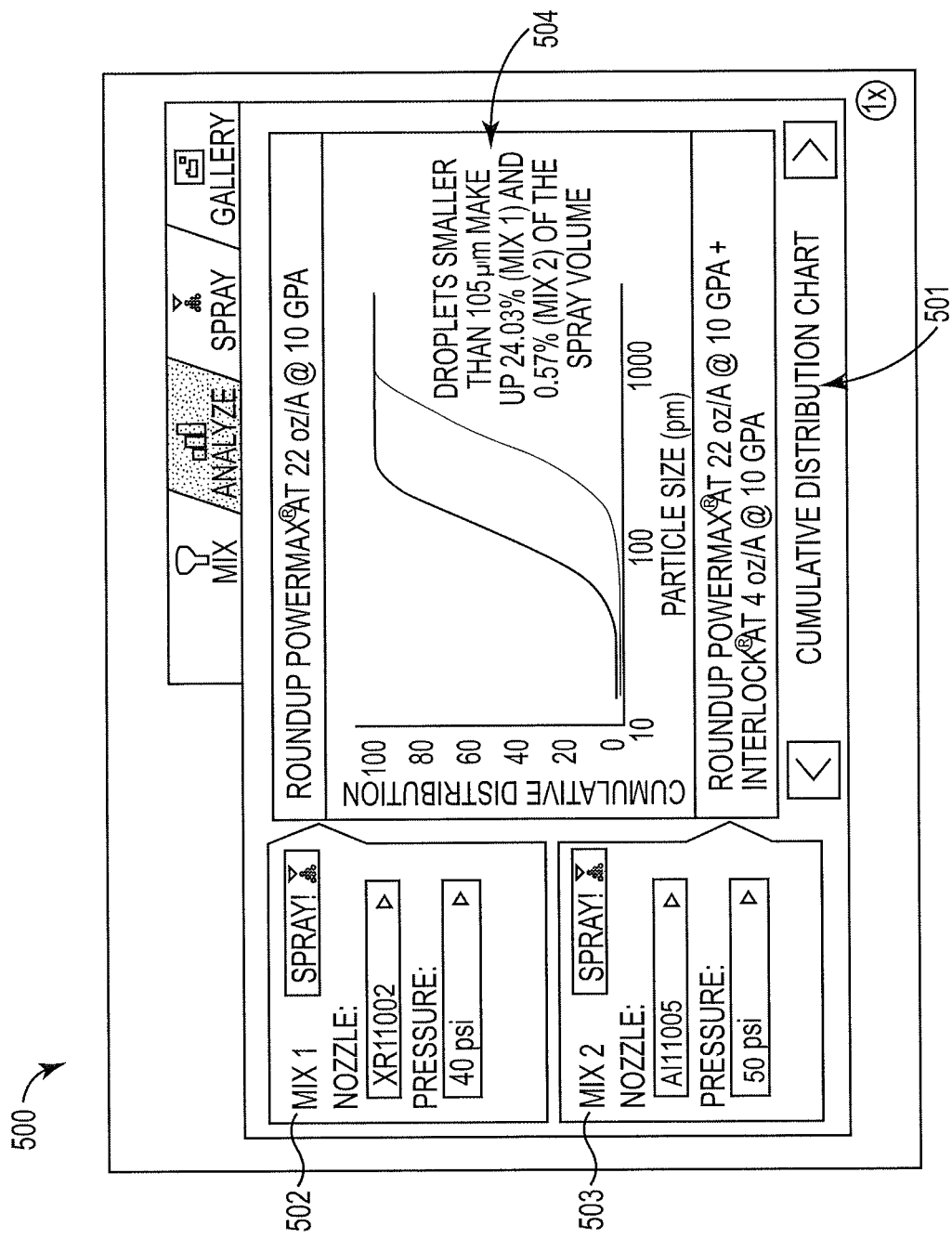
FIG. 5 depicts a user interface for providing a cumulative distribution chart of a first and second spray as a function of particle size versus cumulative distribution.

FIG. 5 depicts a user interface 500 illustrating a cumulative distribution chart 501 of a spray distribution for a first and second spray, "Mix 1" 502 and "Mix 2" 503, as a function of particle size (x-axis) versus cumulative distribution (y-axis). The cumulative distribution chart representing mixes 502, 503 may be provided in connection with aspects of the method 100 of FIG. 1, and user selections of the mixes for displaying the distribution view 501 may be received via the user interface 200 of FIG. 2 for "Mix 1" 502, via a second user interface for "Mix 2" 503, described above, and via user interface 500. For example, in FIG. 5, the spray conditions may be received via the user interface 500 in the same manner described above in connection with entry of spray conditions via the user interfaces 300, 370, and 400 of FIGS. 3A, 3B and 4. Based on receiving two different spray variable selections, the relative amounts of the droplets within the droplet size classes are used to generate a cumulative distribution chart 501 for each of the mixes 502, 503 for simultaneous display. In some implementations, the charts are generated based on data points collected through the spray analysis of the present disclosure. The cumulative distribution chart 501 enables a user to make comparisons of sprays based on their compositions, nozzles and pressures generating the spray, as well as other variables affecting spray. In some aspects, the cumulative distribution chart 501 displays droplet information 504 about the relative amounts of the spray falling within a certain size range or droplet size class. For example, in FIG. 5, droplet information displayed indicates that droplets that are smaller than 105 µm make up 24.03 percent of "Mix 1" and 0.57 percent of "Mix 2." In further aspects, droplet information 504 may be displayed by selecting or "hovering" over the representative droplet. For example, where multiple data points form the lines for the mixes 502, 503, in the distribution chart 501, the data points may be associated with droplet size classes, and by selecting one of the data points, droplet information 504 may be displayed in the manner shown in FIG. 5, or additionally or alternatively, in the manner shown in FIG. 3A in connection with the displayed droplet size information 325.

In addition, the spray variables may be updated based on spray icon selections as described above in connection with FIGS. 3A, 3B and 4, and the user interface 500 may display updated results in response to the selection.

Figure 6:
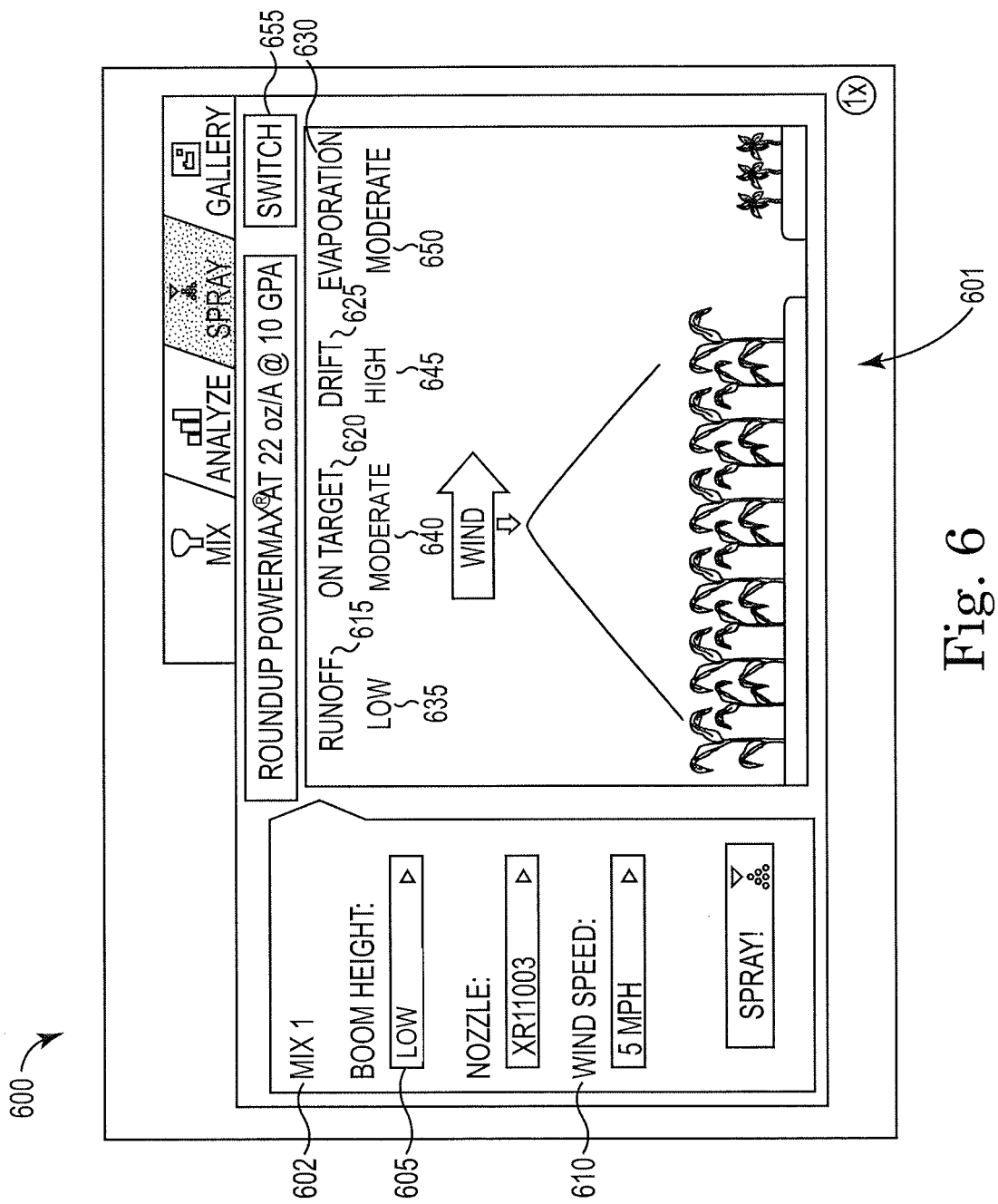
FIG. 6 depicts a user interface for providing a spray view of a spray.

FIG. 6 depicts a user interface 600 showing a spray view 601 of a selected spray, "Mix 1" 602. The spray view 601 may be provided in connection with aspects of the method 100 of FIG. 1, and user selections of spray variables for displaying the spray view 601 may be received via the user interface 200 of FIG. 2 as well as via the user interface 600. The spray view 601 provides a qualitative description of the potential fate of a spray, based, in part, on literature values for environmental factors that may not be accounted for using a closed system. For example, in FIG. 6, these environmental factors include boom height and wind speed, and these variables may be selected using the boom height field 605 and the wind speed field 610. The boom height field 605 enables selections related to a distance from the ground or the crop canopy at which the spray is delivered. For example, the spray may be delivered at about 18 or 36 inches from the crop canopy, where 18 inches may be a low boom height available for selection in the boom height field 605 and 36 inches may be a high boom height available for selection in the boom height field 605. Alternatively, the spray may be delivered to soil or small plants close to the soil and a low boom height selection may represent only a slight elevation from soil, whereas a high boom height selection may represent a relatively higher elevation from the soil. The wind speed field 610 provides selections related to a variety of wind speeds the spray may encounter during application to soil or foliage. For example, the selections may include relatively low wind speeds of 5 miles per hour, or relatively high wind speeds of 10 miles per hour. In contrast to the distribution, volumetric and chart views depicted in FIGS. 3A to 5, in which the sprays are analyzed in a closed system, the results of the analyzed spray displayed in the spray view 601 of FIG. 6 are further based on field studies and modeling.

The spray analysis results depicted in FIG. 6 thus provide information about the fate of the sprayed droplets, and may be characterized based on the predicted droplet response as a function of the composition of the spray, delivery parameters, and one or more environmental parameters. The predicted response areas in FIG. 6 are based on a qualitative description of the droplet fate and include droplet runoff potential 615, on-target potential 620, drift potential 625 and evaporation potential 630. For "Mix 1" 602, the droplet response of the spray is characterized as having a leaf runoff potential of low 635; an on-target potential 620 of moderate 640; a drift potential 625 of high 645; and an evaporation potential of moderate 650. The relative amounts of the spray falling within the predicted response areas may be determined based on the calculated percent of the spray volume falling within the droplet size categories of the present disclosure. For example, droplets with a high potential for leaf runoff may have a size of greater than 550 µm, and this may be true at all wind speeds and boom heights. Droplets with a high potential for on-target application may have a size range of between about 200 µm to about 550 µm, however, higher wind speeds and boom heights may decrease the potential to moderate or low. Droplets with a high potential for drift may be droplets having a size range from about 50 µm to about 200 µm, and high wind speeds and high boom heights may increase the potential for drift. Droplets with a high potential for evaporation may have a size of less than 50 and this may be true at all wind speeds and boom heights.

The user interface 600 enables users to view the various spray mixtures, allows updating of sprays via both user interface 600 and user interface 200, and enables toggling between spray mixes upon selection of the switch icon 655.

The spray analysis information of the present disclosure may be displayed on a computer screen, such as a screen coupled to a PC, a mobile phone, a tablet and so on. Users may enter selections via the user interfaces (e.g., via pull down menus, radio buttons, free text fields and so on) and view the results via the screen. In some aspects, the users may access the spray analysis results using a tablet computer, for example, via a mobile software application. In addition, the system may be modified or updated, for example, based on EPA spray drift regulatory information and leaf coverage information. By providing agricultural spray results in a visually understandable format, the results may be evaluated by the users to understand whether the sprays are acceptable for reaching the intended target or whether the sprays contribute to spray drift, leaf runoff or evaporation.

In the present disclosure, the methods disclosed may be implemented as sets of instructions or software readable by a device. Further, the specific order or hierarchy of steps in the methods disclosed are examples of sample approaches and the specific order or hierarchy of steps in the method can be rearranged while remaining within the disclosed subject matter. The accompanying method claims present elements of the various steps in a sample order, and are not necessarily meant to be limited to the specific order or hierarchy presented.

The present disclosure may be provided as a computer program product, or software, that may include a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on. By means of example and not limitation, FIG. 7 provides a block diagram of a computer system 700 for providing a visual display of spray patterns, according to certain implementations. The system 700 includes a spray analysis and visualization tool 710 with a database 711, a processor 712, a display 713 and an input device 714 (e.g. a keyboard or remote control). In some implementations, the spray analysis and visualization tool 710 may be one or more general purpose computers, special purpose computers or both. In some aspects, the system 100 may be communicatively coupled to a communications network 715 for enabling a number of user devices 716 to enter user input and receive information on the predicted spray performance of the selected from the system 700.

It is believed that the present disclosure and many of its attendant advantages will be understood by the foregoing description, and it will be apparent that various changes may be made in the form, construction and arrangement of the components without departing from the disclosed subject matter. The form described is merely explanatory, and it is the intention of the following claims to encompass and include such changes.

While the present disclosure has been described with reference to various embodiments, it will be understood that these embodiments are illustrative and that the scope of the disclosure is not limited to them. These and other variations, modifications, additions, and improvements may fall within the scope of the disclosure as defined in the claims that follow.

What is claimed is:

1. A computer-implemented method for depicting agricultural spray behavior as a spray distribution, the method comprising:
   using a computer processor configured to:
      receive a selection of an agricultural spray comprising at least one of an active ingredient or an adjuvant;
      receive a selection of a spray parameter at which the agricultural spray is to be sprayed;
      retrieve analyzed spray particulate data based on the received selections, the retrieved data comprising a distribution of relative amounts of agricultural spray droplets within droplet size classes where each class corresponds to a range of droplet sizes; and
   transmitting for graphical display the distribution of the relative amounts of the spray droplets in the droplet size classes;
   wherein the spray droplets are displayed as a series of representative droplets, each representative droplet associated with one of the droplet size classes, and
   wherein the representative droplets within a droplet size class are displayed with droplet size information.

2. The method of claim 1, wherein the representative droplets within a droplet size class are displayed with droplet size information comprising one or more of the range of droplet sizes represented, drift potential, leaf runoff potential and leaf coverage.

3. The method of claim 1, wherein the representative droplets displayed are arranged within a distribution curve representing a distribution of size of the representative droplets based on the relative amounts.

4. A computer-implemented method for depicting agricultural spray behavior, the method comprising:
   using a computer processor configured to:
   receive a selection of an agricultural spray comprising at least one of an active ingredient or an adjuvant;
   receive a selection of one or more spray parameters at which the agricultural spray is to be sprayed;
   retrieve analyzed spray particulate data based on the received selections, the retrieved analysis data comprising relative amounts of agricultural spray droplets within droplet size classes corresponding to a range of droplet sizes; and
   transmitting for graphical display the relative amounts of the spray droplets in the droplet size classes,
   wherein the calculated relative amounts of the droplets are displayed as a series of representative droplets, each representative droplet associated with one of the droplet size classes, and
   wherein the representative droplets within a droplet size class are displayed with droplet size information.

5. The method of claim 4, wherein:
   the received selections of the agricultural spray and the one or more spray parameters comprises a set of selections and the computer processor is configured to receive at least two sets of selections; and
   the relative amounts of the droplets in the droplet size classes for the sets of selections are relative volumes of the droplets in the droplet size classes and are displayed as a volumetric comparison of the sets of selections.

6. The method of claim 4, wherein:
the received selections of the agricultural spray and the one or more spray parameters comprises a set of selections and the computer processor is configured to receive at least two sets of selections; and
the relative amounts of the droplets within the droplet size classes for the sets of selections are simultaneously displayed as a cumulative distribution chart.

7. The method of claim 4, wherein:
the received spray parameter selections comprise one or more of a boom height and a wind speed; and
transmitting for display the relative amounts of the droplets within the droplet size classes within a plurality of spray quality categories associated with the agricultural spray being sprayed according to the received selections of the one or more of the boom height and wind speed.

8. A computer-implemented method for providing agricultural spray information, the method comprising:
using a computer processor configured to:
analyze spray particulate data of sprayed agricultural fluids to identify a droplet size distribution of the sprayed fluids;
group droplets within the droplet size distribution into droplet size classes, each droplet size class representing a range of droplet sizes;
calculate a relative amount of the droplets within the droplet size classes;
receive a selection of an agricultural mixture corresponding to one of the sprayed fluids; and
transmitting for display the calculated relative amounts of the droplets within the droplet size classes for the spray particulate data based on the received selection,
wherein the calculated relative amounts of the droplets are displayed as a series of representative droplets, each representative droplet associated with one of the droplet size classes, and
wherein the representative droplets within a droplet size class are displayed with droplet size information.

9. The method of claim 8, wherein the representative droplets displayed are arranged within a distribution curve representing a distribution of size of the representative droplets based on the relative amounts.

10. The method of claim 8, wherein the droplet size information displayed comprises one or more of a range of droplet sizes represented, drift potential and leaf runoff potential.

11. The method of claim 8, wherein a value representing a span of the distribution is displayed using the computer display, wherein the span is $(X_{90}-X_{10})/X_{50}$.

12. The method of claim 8, wherein a value representing a volume mean diameter (VMD) of the distribution is displayed, wherein the VMD is a median droplet size of the sprayed fluid.

13. The method of claim 8, wherein the droplet size classes are predefined.

14. The method of claim 8, wherein the received selection comprises a set of selections of at least one of an active ingredient or an adjuvant in combination with at least one of a rate of spray, a spray pressure or a nozzle type.

15. The method of claim 14, wherein:
the computer processor is configured to receive two sets of selections and transmit for display the calculated relative amounts of the droplets within the droplet size classes as a volumetric comparison of the two sets of selections.

16. The method of claim 14, wherein:
the computer processor is configured to receive two sets of selections and transmit for display the relative amounts of the droplets within the droplet size classes for each of the sets of selections as a cumulative distribution chart.

17. The method of claim 14, wherein:
the received user selection further comprises a selection of at least one of a boom height or a wind speed; and
transmitted for display are the relative amounts of the droplets within the droplet size classes within a plurality of spray quality categories associated with the agricultural spray according to the received selections.

18. The method of claim 17, wherein the spray quality categories are based on one or more of leaf runoff, on-target spray, drift potential and evaporation.

19. The method of claim 18, wherein one or more of the droplet size classes are defined based on the spray quality categories.

20. The method of claim 8, wherein the droplet size information displayed comprises leaf coverage.

\* \* \* \* \*

UNITED STATES PATENT AND TRADEMARK OFFICE
CERTIFICATE OF CORRECTION

| | |
|---|---|
| PATENT NO. | : 9,098,732 B2 |
| APPLICATION NO. | : 13/734571 |
| DATED | : August 4, 2015 |
| INVENTOR(S) | : Lillian C. Magidow |

It is certified that error appears in the above-identified patent and that said Letters Patent is hereby corrected as shown below:

SPECIFICATION

| Column | Line | | Should Be |
|---|---|---|---|
| 11 | 2 | "a size of less than 50 and this" | -- a size of less than 50 μm, and this -- |

Signed and Sealed this
Ninth Day of February, 2016

Michelle K. Lee
*Director of the United States Patent and Trademark Office*